(12) United States Patent
Bengs et al.

(10) Patent No.: US 6,548,075 B1
(45) Date of Patent: Apr. 15, 2003

(54) COSMETIC OR MEDICAL PREPARATION FOR TOPICAL USE

(75) Inventors: Holger Bengs, Frankfurt (DE); Arnold Schneller, Messel (DE); Jürgen Grande, Bad Soden (DE); Silke Schuth, Ruppach-Goldhausen (DE); Gitte Böhm, Frankfurt (DE); Alfred Braunagel, Mainz (DE)

(73) Assignee: Celanese Ventures GmbH (DE)

( * ) Notice: Subject to any disclaimer, the term of this patent is extended or adjusted under 35 U.S.C. 154(b) by 0 days.

(21) Appl. No.: 09/869,399

(22) PCT Filed: Nov. 30, 1999

(86) PCT No.: PCT/EP99/09293

§ 371 (c)(1),
(2), (4) Date: Nov. 14, 2001

(87) PCT Pub. No.: WO00/38623

PCT Pub. Date: Jul. 6, 2000

(30) Foreign Application Priority Data

Dec. 28, 1998 (DE) .......................... 198 60 371

(51) Int. Cl.⁷ .......................... A61K 6/00; A61K 7/00; A61K 7/04
(52) U.S. Cl. .......................... 424/401; 424/64
(58) Field of Search .................. 424/401, 64

(56) References Cited

U.S. PATENT DOCUMENTS 5,726,161 A * 3/1998 Whitstler ...................... 514/54

FOREIGN PATENT DOCUMENTS

| DE | 41 20 760 | 4/1993 |
|---|---|---|
| DE | 197 37 481 A1 | 3/1999 |
| DE | 198 03 415 A1 | 8/1999 |
| DE | 198 16 070 A1 | 10/1999 |
| DE | 198 27 978 A1 | 12/1999 |
| DE | 198 30 618 A1 | 1/2000 |
| DE | 198 39 216 | 1/2000 |
| DE | 198 39 212 A1 | 5/2000 |
| DE | 198 39 214 A1 | 5/2000 |
| DE | 198 52 826 A1 | 5/2000 |
| FR | 2 747 306 | 10/1997 |
| GB | 2 247 242 | 2/1992 |
| JP | 61161213 | 7/1986 |
| WO | WO 95 31553 | 11/1995 |
| WO | WO 97 28780 | 8/1997 |
| WO | WO 99 11695 | 3/1999 |
| WO | WO 00 12589 | 3/2000 |
| WO | WO 00 12617 | 3/2000 |

OTHER PUBLICATIONS

Eggensperger, M. et al., "Multiactive polysaccharides, part 1—fungal extracts" [Multiaktivwirksame Polysaccharides, Teil I—Pilzestrakte]; SÖFW–Journal, vol. 123, Aug. 1997: 542–546.

Zülli, F. et al., "CM–Glucan: a biological response modifier from Baker's Yeast for Skin Care"; SÖFW–Journal, vol. 123, Aug. 1997: 535–541.

Citernesi, U. et al., "Cyclodextrins in functional dermocosmetics;" Cosmetics & Toiletries, vol. 110, Mar. 1995: 64–61.

*German Pharmacopeia*, Wissenschaftliche, Verlagsgesellschaft mbH, Stuttgart, Govi–Verlag GmbH, Frankfurt, 9$^{th}$ ed., 1987. (German).

Leaflet; "Cosmetics—ingredients—functions;" Industrieverband Körperpflege und Waschmittel e.V. and Fachverband der Chemischen Industrie Österreichs, Berufsgruppe Körperpflegemittel, Frankfurt am Main/Vienna, Jun. 1998. (German).

Search Report of Apr. 14, 2000.

Inaba, R. et al. "Application of Porous Starch Complex Poweder" J. SCCJ (1995) 29 (2) p. 146–153, Abstract.

* cited by examiner

Primary Examiner—Thurman K. Page
Assistant Examiner—S. Howard
(74) Attorney, Agent, or Firm—Gilberto M. Viliacorta; Serge Sira; Katten Muchin Zavis Roseman

(57) ABSTRACT

The present invention relates to a topical preparation containing spherical microparticles as the essential component, wherein the microparticles comprise water-insoluble linear polyglucan.

18 Claims, No Drawings

COSMETIC OR MEDICAL PREPARATION FOR TOPICAL USE

This application is a 371 of PCT/EP99/09293 filed Nov. 30, 1999.

DESCRIPTION

The present invention relates to a cosmetic or medicinal preparation for topical application, in particular a skincare composition, comprising spherical microparticles which consist entirely or partially of at least one linear water-insoluble polyglucan, and the use of spherical microparticles which consist entirely or partially of at least one linear water-insoluble polyglucan in preparations of this type. In particular, the present invention relates to a cosmetic or medicinal preparation for topical application which on application imparts a particularly pleasant soft feel.

The use of polysaccharides based on starch, such as polyglucans, for cosmetic purposes has been known since time immemorial.

Recently, polysaccharide products for cosmetic and therapeutic purposes have been increasingly developed which have specific property profiles. Thus a high caring action for irritated, dry skin is described by H. Eggensperger, M. Wilker in SÖFW-Journal, 123, issue August 1997, pages 542 to 546, "Multiaktivwirksame Polysaccharide, Teil I—Pilzestrakte [Multiactive polysaccharides, part I—Fungal extracts]" for beta-polyglucans from fungi such as yeasts and their carboxymethylated derivatives. Particularly advantageous effects on the skin were demonstrated for beta-1,3-polyglucans having beta-1,6 linkages for which additionally immunostimulating action and tumor activity was observed (loc. cit., F. Züll et all., loc. cit., pages 535 to 541).

Cyclodextrins, cyclic alpha-, beta- or gamma-1,4,-oligosaccharides having 6 to 8 glucan units, are also increasingly used for functional skincare, since they form inclusion compounds with a large number of active compounds and caring substances and can thereby bring about a delayed release of these substances at the application site (U. Citernesi, M. Scaiacchitano in Cosmetics and Toiletries magazine, vol. 110, March 1995, pages 53 to 61 "Cyclodextrins in functional Dermocosmetics").

Although a large number of products are known for all sorts of cosmetic and medicinal intended uses, there is a constant need for novel improved products. Products are in particular desirable which, on application to the skin, produce a pleasant feel and impart a smooth, soft impression.

Products of this type are advantageous for application in the case of sensitive skin and are especially also suitable for the production of medicinal preparations for topical application.

It has been shown that preparations for topical application (subsequently also called topical preparation) impart a particularly pleasant, soft feel on application if spherical microparticles are added to them which consist entirely or partially of linear water-insoluble polyglucans.

According to the invention, a preparation for topical application is thus made available which contains spherical microparticles which consist entirely or partially of at least one linear water-insoluble polyglucan.

Preparations for topical application are understood within the meaning of the invention very generally as meaning cosmetic compositions, i.e. bodycare compositions and decorative cosmetics. According to the invention, the term also includes human and veterinary medicinal preparations which are applied externally.

Preparations according to the invention can be creams, compact creams, lotions, masks, powders in any desired form, e.g. liquid, loose, compact, particulate etc., ointments, ointment bases, soaps etc. for decorative, caring or medicinal application.

Examples of the decorative cosmetics are creams, powders or foundations for make-up, e.g. rouge, eyeshadow, lipsticks.

Essential for the achievement of this object is the use according to the invention of the spherical microparticles, which consist entirely or partially of at least one water-insoluble linear polyglucan.

Microparticles of this type are distinguished by a high uniformity in size and shape. Moreover, they can easily form stable suspensions themselves without addition of dispersant aids, which is particularly advantageous for the production of the preparations according to the invention if they are based on emulsions.

The microparticles employed according to the invention are furthermore distinguished by high biocompatibility.

The naturally identical character of the water-insoluble linear polyglucans used for the preparation and of their degradation products is in particular of high importance for the biocompatibility of the microparticles employed according to the invention.

Spherical microparticles are understood as meaning microparticles which have approximately spherical shape. In the case of description of a sphere by axes of equal length starting from a common origin and directed into space, which define the radius of the sphere in all spatial directions, a difference in the lengths of the axes of 1% to 40% from the ideal state of the sphere is possible for the spherical particles. Preferably, the difference is 25% or less, particularly preferably 15% or less.

The microparticles can have a mean diameter Dn (numerical average value) of 1 nm to 100 μm, preferably of 50 nm to 10 μm, and particularly preferably of 100 nm to 3 μm.

The surface of the spherical particles can be compared macroscopically with a raspberry, the depth of irregularities on the particle surface, such as dents or clefts, being at most 20%, preferably 10%, of the mean diameter of the spherical microparticles.

The specific surface area of the microparticles is in general from 1 m$^2$/g to 100 m$^2$/g, preferably 1.5 m$^2$/g to 20 m$^2$/g and particularly preferably 3 m$^2$/g to 10 m$^2$/g.

The particles according to the invention further preferably exhibit a dispersity D=weight-average value of the diameter ($d_w$)/numerical average value of the diameter ($d_n$) of 1.0 to 10.0, in particular of 1.5 to 5.0 and particularly preferably of 2.0 to 3.0.

The mean values used here are defined as follows:

$d_n$=sum of $n_i \times d_i$/sum of $ni$=numerical average value $d_w$=sum of $n_i \times d_i^2$/sum of $n_i \times d_i$=weight-average value where $n_i$=number of particles of diameter $d_i$, $d_i$=a determined diameter, i=constant parameter.

Microparticles can also be employed for the present invention whose surface has been modified, e.g. by derivatization of functional groups, such as hydroxyl groups of the polyglucans.

Linear water-insoluble polyglucans within the meaning of the present invention are polysaccharides which are constructed from glucans as monomeric structural units, such that the individual units are always linked to one another in the same manner. Each base unit or structural unit defined in this way has exactly two linkages, in each case one to another monomer. Excluded from this are only the two base units which form the beginning or the end of the polysaccharide.

These have only one linkage to a further monomer and form the end groups of the linear polyglucan.

If the base unit has three or more linkages, this is referred to as branching. The 'degree of branching' results here from the number of hydroxyl groups per 100 base units which are not involved in the synthesis of the linear polymer backbone and which form branchings.

According to the invention, the linear water-insoluble polyglucans have a degree of branching of at most 8%, i.e. they have at most 8 branchings to 100 base units. The degree of branching is preferably less than 4% and in particular at most 2.5%.

Polyglucans are particularly preferred whose degree of branching in the 6-position is less than 4%, preferably at most 2% and in particular at most 0.5%, and in the other positions, e.g. in the 2- or 3-position, is preferably in each case at most 2% and in particular 1%.

Polyglucans are in particular suitable for the invention which have no branching, or whose degree of branching is so minimal that it is no longer detectable using conventional methods.

Examples of preferred water-insoluble linear polyglucans are linear poly-D-glucans, where the nature of the linking is insignificant as long as linearity within the meaning of the invention is present. Examples are poly-alpha-D-glucans, in particular poly-1,4-alpha-D-glucan and poly-1,3-beta-D-glucan, poly-1,4-alpha-D-glucan being particularly preferred.

For the present invention, the prefixes "alpha", "beta" or "D" only relate to the linkages which form the polymer backbone and not to the branchings. For the present invention, the term "water-insoluble polyglucan" is understood as meaning compounds which, according to the definition of the German Pharmacopeia (GP=German Pharmacopeia, Wissenschaftliche Verlagsgesellschaft mbH, Stuttgart, Govi-Verlag, Frankfurt, edition 1987) corresponding to classes 4 to 7 come under the categories "not very soluble", "poorly soluble", very poorly soluble" or "virtually insoluble" compounds.

In the case of the polyglucans used according to the invention, this means that at least 98% of the amount employed, in particular at least 99.5%, is insoluble under normal conditions (T=25° C.+/−20° C., p=101325 Pascals +/−20%) in water (corresponding to classes 4 and 5).

For the present invention, poorly soluble to virtually insoluble compounds, in particular very poorly soluble to virtually insoluble compounds, are preferred.

"Very poorly soluble" corresponding to class 6 can be demonstrated by the following experiment description: One gram of the polyglucan to be investigated are heated to 130° C. under a pressure of 1 bar in 1 l of deionized water. The resulting solution remains stable only briefly for a few minutes. On cooling under normal conditions, the substance precipitates again. After cooling to room temperature and separation by means of centrifugation, at least 66% of the amount employed can be recovered taking into account the experimental losses.

The polyglucans employed according to the invention can be of any desired origin as long as the conditions indicated above with respect to the terms "linear" and "water-insoluble" are fulfilled.

They can be obtained naturally or biotechnologically.

For example, they can be obtained by isolation and/or purification from natural plant or animal sources.

Sources can also be used which have been genetically manipulated such that, in comparison with the unmanipulated source, they contain a higher proportion of unbranched or comparatively slightly branched polyglucans.

They can have been prepared from nonlinear poly-alpha-glucans by enzymatic or chemical debranching. Here, nonlinear polyglucans which contain branchings can be treated with an enzyme in such a way that cleavage of the branching occurs, such that after their removal linear polyglucans are present. These enzymes can be, for example, amylases, isoamylases, gluconohydrolases, cyclomaltodextrin glucanotransferases or pullulanases.

Biotechnical methods include biocatalytical processes, also biotrans-formational processes, or fermentative processes.

Linear polyglucans prepared by biocatalysis (also biotransformation) in the context of this invention means that the linear polyglucan is prepared by catalytic reaction of monomeric base units such as oligomeric saccharides, e.g. of mono- and/or disaccharides, by using a 'biocatalyst', customarily an enzyme, under suitable conditions. Reference is also made in this connection of "in-vitro biocatalysis".

In the linguistic usage of the invention, linear poly-alpha-glucans from fermentations are linear poly-alpha-glucans which are obtained by fermentative processes using organisms occurring in nature, such as fungi, algae, bacilli, bacteria or protists or using organisms not occurring in nature, but natural organisms modified with the aid of genetic methods of general definition, such as fungi, algae, bacilli, bacteria or protists or can be obtained with switching-on and assistance of fermentative processes. Reference is also made in this connection to "in-vivo biocatalysis".

Examples of microorganisms of this type are *Piichia pastoris, Trichoderma Reseii, Straphylococcus Carnosus, Escherichia Coli* or *Aspergillus Niger.*

Advantageous processes for biotechnological production are described, for example, in WO 95/31553 or the previously unpublished German patent application of the applicant having official reference 198 27 978.5.

According to WO 95/31553, amylosucrases are used for the preparation of linear water-insoluble polyglucans such as poly-1,4-α-D-glucan by means of a biocatalytic process. Further suitable enzymes are polysaccharide synthases, starch synthases, glycol transferases, 1,4-α-D-glucan transferases, glycogen synthases or alternatively phosphorylases.

Modified water-insoluble linear polyglucans can also be employed, it being possible for the polyglucans to have been modified, for example, by esterification and/or etherification in one or more positions not involved in the linear linkage. In the case of the preferred 1,4-linked polyglucans, the modification can take place in the 2-, 3- and/or 6-position.

Modification within the meaning of the invention means that the hydroyl groups which are not involved in the linkage are chemically modified. This excludes reopening of the glucan units such as takes place, for example, on oxidative carboxylation or hydrolysis. Measures for modifications of this type are adequately known to the person skilled in the art.

Thus linear polyglucans such a pullulans, which are water-soluble per se, can be rendered water-insoluble by modification.

For the present invention, water-insoluble linear polyglucans are preferably employed which have been prepared in a biotechnological process, in particular in a biocatalytical or a fermentative process.

In contrast to polyglucans, which are isolated from natural sources, such as plants, the linear water-insoluble polyglucans obtained here have a particularly homogeneous property profile, e.g. with respect to the molecular weight distribution, they contain no undesired by-products which have to be separated off in a complicated manner or could cause allergic reactions or contain them at most only in very small amounts, and can be reproduced in exactly specified form in a simple manner. In particular, using biotechnological methods water-insoluble linear water-insoluble polyglucans can be obtained, such as the preferred poly-1,4-α-D-glucans, which contain no branchings, or whose degree of branching is below the limit of detection of conventional analytical methods.

The polyglucans can further be employed in the form of 'alpha-amylase-resistant polyglucans' such as are described by way of example of poly-1,4-a-D-glucan in the previously unpublished German patent application, having official reference 198 30 618.0, of the applicant.

Alpha-amylase-resistant polyglucans can be obtained by preparation of a suspension or dispersion from water-insoluble polyglucans and water, warming the suspension or dispersion to a temperature in the range from 50 to 100° C., allowing the paste-like mixture to cool to a temperature in the range from 50° C. down to the freezing point, preferably 35 to 15° C., 27 to 22° C., 16 to 0° C. or 6 to 2° C., over a period of 1 to 72 h, preferably 1 to 36 h and in particular 15 to 30 h, and retrogradation of the paste-like mixture at a temperature which is reduced relative to the temperature of the heated paste-like mixture in a temperature range from 90 to 4° C. and, if appropriate, drying or dehydration of the product obtained.

The polyglucan can also be employed as a thermoplastic polyglucan which is obtainable by melting linear water-insoluble polyglucan and adding at least 20% by weight, preferably at least 30% by weight, of a plasticizer such as sorbitol, glycerol, their condensation products and oligomers, DMSO, succinic acid, citric acid monohydrate, malic acid, tartaric acid etc. at about 170° C.

The previously unpublished German patent application of earlier priority having official reference 198 52 826, to which reference is expressly made for the purposes of this description, gives a description of suitable measures and properties of thermoplastic polyglucans as exemplified by the preferred linear water-insoluble poly-1,4-α-D-glucan.

The molecular weights $M_w$ (weight average, determined by means of gel-permeation chromatography in comparison with a calibration using pullulan standard) of the linear polyglucans used according to the invention can vary within a wide range from $0.75 \times 10^2$ g/mol to $10^7$ g/mol. Preferably, the molecular weight $M_w$ lies in a range from $10^3$ g/mol to $10^6$ g/mol and particularly preferably from $10^3$ g/mol to $10^5$ g/mol. A further advantageous range is from $2 \times 10^3$ to $8 \times 10^3$. Corresponding ranges apply to the preferably employed poly(1,4-α-D-glucan).

The molecular weight distribution or polydispersity $M_w/M_n$ can likewise be varied within wide ranges, depending on the process of preparation of the polyglucan. Preferred values are from 1.01 to 50, in particular from 1.01 to 15. Polyglucans with little polydispersity, e.g. from 1.01 to 2.5, are particularly preferred.

The polydispersity increases here with a bimodal distribution of the molecular weights.

For the preparation of the microparticles, it is possible to use a single polyglucan, in particular poly-1,4-D-glucan and very particularly poly-1,4-α-D-glucan or mixtures of two or more representatives.

In a further embodiment, it is possible to add a water-insoluble branched polysaccharide, preferably a polyglucan, in particular a poly-1,4-alpha-D-glucan or poly-1,3-beta-D-glucan. It is also possible to add mixtures of two or more branched polysaccharides.

The branched polysaccharides can be of any desired origin. In this connection, reference is made to the relevant explanations for the linear water-insoluble polyglucans. Preferred sources are starch and starch analogs such as glycogen. If necessary, the proportion of linear structures in the branched polysaccharides can be increased by suitable enrichment processes.

The same details for the water insolubility apply as for the linear water-insoluble polyglucan, the molecular weights can also be higher for the branched polysaccharides, e.g. have values up to preferably $10^9$ g/mol and more.

It is also possible to admix other polymers, in particular biocompatible or biodegradable polymers. The amount of the polymer or the other polymers which are admixed here always depends, without the spherical shape and/or other properties of the microparticles to be prepared being modified, on the polymer added.

To ensure the desired properties of the microparticles, the proportion of linear water-insoluble polyglucan should be at least 70% by weight, in particular 8% by weight and preferably 90% by weight, based on the total content of linear water-insoluble polyglucan including optionally branched polysaccharide and, if appropriate, further polymers.

According to a particularly preferred embodiment, the microparticles consist to 100% of linear water-insoluble polyglucan, in particular linear water-insoluble poly-1,4-α-D-glucan, which has preferably been obtained biocatalytically.

Examples of processes for the preparation of the microparticles are the precipitation process or spray-drying process.

The spherical microparticles can be prepared by dissolving the water-insoluble linear polyglucan or a mixture of a number of them and, if appropriate, further polymers in a solvent, e.g. DMSO, introducing the solution into a precipitating agent, e.g. water, preferably at a temperature of 20° C. to 60° C., if required cooling the solution to a temperature of minus 10° C. to plus 10° C. and separating off the particles formed in this process.

The process of dissolving the polyglucan used as starting material can be carried out here at room temperature or higher temperatures.

The concentration of linear water-insoluble polyglucan including optionally branched polysaccharide and further polymers in the solvent can, if required, be varied within wide limits. It is preferably in a range from 0.02 g/ml to 1.0 g/ml, in particular from 0.05 g/ml to 0.8 g/ml and particularly preferably from 0.3 g/l to 0.6 g/l.

Examples of precipitating agents are water, dichloromethane, a mixture of water and dichloromethane, mixtures of water and alcohols such as methanol, ethanol, isopropanol, water and a mixture of water and dichloromethane being particularly preferred.

Preferably, the ratio of solvent to precipitating agent is selected in a range from 1:1000 to 1:4 (part of solvent/parts of precipitating agent), preferably 1:100 to 1:10 and in particular 1:70 to 1:30.

In general, it is unimportant here in what sequence the solvent and the precipitating agent are combined, e.g. whether the precipitating agent is added to the solvent or conversely. It is important, however, that rapid mixing is guaranteed.

The precipitation process can be carried out relatively slowly at low temperature overnight.

It can be influenced and controlled by variation of the temperature and of the precipitating agent. If it is cooled, it must be ensured that the mixture of solvent and precipitating agent remains liquid and does not solidify.

By concomitant use of suitable additives, influence can be brought to bear on the properties of the microparticles such as size, surface structure, porosity etc. and on the carrying-out of the process.

Suitable additives are, for example, surface-active substances such as sodium dodecylsulfate, N-methylgluconamide, polysorbates (e.g. Tween (registered trade mark)), alkyl polyglycol ethers, ethylene oxide/propylene oxide block polymers (e.g. Pluronic (registered trade mark)), alkyl polyglycol ether sulfates, generally alkyl-sulfates and fatty acid glycol esters, and sugars such as fructose, sucrose, glucose, water-soluble cellulose or hot water-soluble poly-alpha-D-glucan, e.g. native or chemically modified starches, poly-alpha-Dglucans obtained from these starches and compounds analogous to starch.

Customarily, these additives are added to the precipitating agent. The amount used depends on the specific individual case and the desired particle properties, the determination of the amount which is advantageous in each case being familiar to the person skilled in the art.

By addition of water-soluble cellulose derivatives to the precipitating agent, microparticles having a particularly smooth surface can be obtained, the depth of the irregularities on the surface of the microparticles in general being at most 10% of the mean diameter.

Examples of water-soluble cellulose derivatives are cellulose esters and cellulose ethers, their mixed forms such as hydroxypropylmethylcelluloses, hydroxyethylcelluloses, carboxymethylcelluloses, cellulose acetates, cellulose butyrates, cellulose propionates, cellulose acetobutyrates, cellulose acetopropionates, cellulose nitrates, ethylcelluloses, benzylcelluloses, methylcelluloses etc.

Mixtures of various water-soluble cellulose derivatives can also be employed.

The term "water-soluble cellulose derivatives" is understood for the present invention as meaning compounds which come under the category very easily soluble to poorly soluble according to the definition of the German Pharmacopeia (GP=German Pharmacopeia, Wissenschaftliche Verlagsgesellschaft mbH, Stuttgart, Govi-Verlag GmbH, Frankfurt, 9th edition, 1987).

The concentration of the water-soluble cellulose derivative in the precipitating agent is any more critical. The upper limit follows inevitably from the resulting viscosity and thus the processibility of the resulting solution.

Concentrations of 2 g (cellulose derivative)/l (precipitating agent) to 150 g/l, preferably from 5 g/l to 80 g/l and in particular 8 g/l to 20 g/l, have proven advantageous.

The proportion of particularly small particles having a mean diameter of 1 nm to 2 μm can be increased by adding hot-water-soluble poly-alpha-D-glucan to the precipitating agent.

The same poly-alpha-D-glucan compounds can be employed for this as have also been mentioned in connection with the linear water-insoluble polyglucan, provided these fulfill the criterion of being soluble in hot water.

Preferred examples are native or chemically modified starches, poly-alpha-D-glucans obtained from these starches, and compounds analogous to starch.

Compounds analogous to starch are understood as meaning compounds which consist of poly-alpha-D-glucans, but are of nonvegetable origin. An example of this is glycogen or dextran. The hot-water-soluble poly-alpha-D-glucans can be employed as a mixture of a linear and a branched component, such as is present, for example, in starch. In this case, the proportion of linear poly-alpha-D-glucan should be more than 15% by weight, preferably 50 to 99.5% by weight, in particular 60 to 90% by weight and very particularly preferably 65 to 80% by weight, based on the total amount of polyalpha-D-glucan in the precipitating agent.

However, they can also consist of branched structures, such as are present, for example, in amylopectin or in glycogen.

In the context of the present invention, "hot-water-soluble" means that the polyalpha-D-glucans are essentially insoluble at room temperature, the same standard applying as for the term "water-insoluble" in connection with linear polysaccharides. The term "solution" or "solubility" is in particular also understood as meaning suspensions or the formation of suspensions such as occur in the dissolution of starch.

For example, the hot-water-soluble starches preferred according to the invention exhibit as good as no solubility in water at room temperature, while the 'cold-water-soluble starches' are more readily soluble under these conditions.

The hot-water-soluble starches are characterized in particular in that they form solutions on heating under autogenous pressure, e.g. in an autoclave, to a temperature in the range from approximately 100 to approximately 160° C., the respective temperature depending on the nature of the starch.

For example, potato starch can be boiled at about 100° C. until it dissolves completely, while cornstarch requires a temperature of about 125° C.

For the process according to the invention, the hot-water-soluble poly-alpha-D-glucans are added to the precipitating agent preferably in maximum concentration, i.e. a saturated solution is prepared. Further suitable ranges are from more than 0.001% by weight to 10% by weight, preferably from 0.01 to 2% by weight and in particular from 0.05% by weight to 0.5% by weight, based on the amount of precipitating agent employed.

In the case of thermoplastic polyglucans, the additives can advantageously be mixed into the thermoplastic mixture as plasticizers or in addition to the plasticizers such that a dry powder mixture is present, which can then be processed to give the microparticles, it being possible for the process of formation of the microparticles to take place also only in the final recipe with mixing-in of the thermoplastic polyglucans.

A detailed description of the microparticles used here, their preparation and the water-insoluble linear polyglucans which can be employed therefor are found in the previously unpublished German patent applications of the applicant, of earlier priority, having references 197 37 481.6, 198 03 415.6, 198 16 070.4, 198 30 618.0, 198 27 978.7 and 198 39 214.1, 198 39 216.8 and 198 39 212.5, to which reference is made for the present description. The three last-mentioned applications are in particular concerned with the modification of the particle condition such as size and surface roughness.

Depending on the intended use, the preparations according to the invention can contain suitable further ingredients customary for the respective use.

Examples of ingredients of this type such as can in particular also be used for cosmetic compositions are emulsifiers, oils, waxes, fats or other customary constituents of a cosmetic formulation such as alcohols, polyols, polymers, foam stabilizers, electrolytes, oils, volatile hydrocarbons, silicone oils or silicone derivatives, active compounds, moisturizers, fillers, color pigments, gloss pigments, colorants, UV filters, perfume oils, antioxidants, stabilizers, anti-inflammatory additives, circulation-promoting additives, preservatives, bactericides, substances having deodorant activity, antiperspirants, insect repellants, vitamins, proteins, agents for preventing foaming, thickeners, emollient substances, moistening and/or moisturizing substances, etc. The leaflet "Kosmetika-Inhaltstoffe-Funktionen"[Cosmetics-ingredients-functions], which has been published by the Industrieverband Körperpflege- und Waschmittel e.V. and the Fachverband der chemischen Industrie Österreichs, Berufsgruppe Körperpflegemittel, Frankfurt am Main/Vienna, June 1998, contains an index of possible permitted ingredients for cosmetic compositions, as can in principle also be used for the present invention.

As a rule, medicinal topical preparations contain one or more medicaments in efficacious concentration.

To differentiate between cosmetic and medicinal use and the corresponding products, reference is made to the regulations in force in Germany, such as are laid down, for example, in the cosmetics directive or the food and drugs act.

It is understood the medicinal preparations can contain the same ingredients as have been mentioned above by way of example for cosmetic use, provided they are permitted for medicinal purposes.

In general, the respective ingredients are added to the preparations according to the invention in amounts customary for the respective intended use.

The microparticles employed according to the invention are also particularly highly suitable as a carrier material for ingredients to be added to the preparations. For example, cosmetic and/or medicinal active compounds can be adsorbed on the microparticles or be present encapsulated in these.

The microparticles can in this case be equipped for the delayed release of the substances incorporated in them. In this regard, reference is also made to the previously unpublished application of the applicant having the official reference 198 16 070.4.

The preparations according to the invention can be prepared according to the customary rules familiar to the person skilled in the art. The preparations according to the invention can be present in any desired formulation suitable for the respective intended use, e.g. as emulsions such as O/W emulsions, W/O emulsions, multiple emulsions e.g. W/O/W, O/W/O, O/W/O/W, W/O/W/O emulsions etc., wax-based, anhydrous, hydrodispersions, gels, oils, anhydrous ointments or ointment bases etc.

The addition of the microparticles used according to the invention to topical preparations lead to an increase in the feel of softness on the skin.

The reason for this soft, smooth sensory feel on the skin is presumed to be in the regular spherical shape of the microparticles, which brings about a rolling effect, similarly to a ball-bearing. They are therefore in particular also suitable as fillers for specific cosmetic effects, if, for example, a particularly soft, smooth powdery effect is to be achieved, in addition they impart to the skin a soft matt appearance similar to the soft focus effect in photography.

In contrast to many pigments such as nonmicronized titanium dioxide, the microparticles employed according to the invention do not whiten on the skin, i.e. they act as transparent and can therefore advantageously replace pigments of this type.

They can thus be taken as a replacement for substances such as talc or kaolin, which on account of their irregular or flake-like shape lead to a dull feeling on application, e.g. in pigmented products or as compaction aids in pressed powders.

An absorbent effect was further observed for the microparticles. On account of this absorbent effect, they are particularly highly suitable also as an additive in deodorants, body powders such as body talc, for the absorption of excess skin fat, e.g. in anti-oil or antiacne products.

It was further observed that they are able to reduce skin roughness, by and large have a soothing effect on the skin, and exert an emollient and moisturizing action.

In addition to the cosmetic effects, the microparticles employed according to the invention are outstandingly dispersible and form stable dispersions or suspensions even without addition of dispersing agents.

A good dispersibility is advantageous, since the addition of dispersing aids and the like can be dispensed with and particularly skin-compatible preparations can be obtained, which are moreover simpler and therefore cheaper to prepare.

Suitable proportions of microparticles for creams, lotions, make-up, compact creams and the like are in the range from approximately 0.5% by weight to approximately 40% by weight, preferably approximately 2 to approximately 10% by weight, for powders from approximately 0.5 to approximately 80% by weight, for ointments and pharmaceutical ointments appropriate amounts can be employed (the amounts are in each case based on the total weight of the preparation concerned).

It is understood that if required, for example for special applications, even more, e.g. 100% by weight or less, of microparticles can be employed.

The amount of microparticles in the preparations depends, of course, on the desired effect and/or the specific formulation of the preparation.

The invention is illustrated below with the aid of individual examples.

EXAMPLES 1 AND 2 AND COMPARATIVE EXAMPLES 1 AND 2

Preparation Procedure for Lotion and Cream

The composition for the lotion (examples 1a, 1b and comparative example 1) and the cream (examples 2a, 2b and comparative example 2) are shown in table 1.
Preparation:
Fat phase:
 Warm emulsifiers and oils to 70° C. with stirring. Add preservatives (parabens) and dissolve with stirring.
Water phase:
 Warm demin. water to 70° C., dissolve remaining constituents with stirring, disperse microparticles.
Preservative solution:
 Dissolve preservative (imidazolidinyl urea) in demin. water.
Preparation:
 Introduce fat phase, t=68–70° C. Add water phase (t=68–70° C.) with stirring and homogenization. After the addition stir for 20 min and homogenize, t=65–68° C.
Cooling:
 With stirring to 40° C.
 Add preservative solution and perfume oil and stir for 5 min and homogenize.
 Cool to 30° C. with stirring.

In relation to the preparations without microparticles, a marked improvement in the softness and smoothness and a velvety feel on application was observed for the creams and lotions according to the invention.

The addition of microparticles led to no whitening on the skin.

EXAMPLES 3a AND b AND COMPARATIVE EXAMPLE 3

Preparation Procedure for Compact Cream Make Up

The composition is given in table 2.
Preparation:
Warm lanolin and oils to a 80–82° C. Dissolve antioxidant and film-forming agent with stirring. Add premolten wax (t=80° C.).
Preparation:
Add premix of color pigments, titanium dioxide, talc, mica and microparticles with stirring and homogenization.

Then stir for 30 min and homogenize, t=82° C.
Emptying:
Empty bulk air-free into suitable containers.
In comparison to the base recipe, the preparation according to the invention showed a reduced waxiness. The addition of 5% by weight of microparticles caused a pleasant powdery feel on removal.

EXAMPLES 4a AND b AND COMPARATIVE EXAMPLE 4

Preparation Procedure for Foundation

The composition is given in table 3.
Preparation:
Warm emulsifier, consistency imparter and oil to 70° C. and mix. Add preservative and dissolve with stirring.

Warm demin. water and propylene glycol to 70° C., dissolve active compound and stabilizer with stirring, suck in premix of color pigments, titanium dioxide and microparticles with homogenizer running. Then stir for 30 min and homogenize.

Preparation:

Suck in filtered fat phase (t=70° C.) with stirring and homogenization and stir for a further 10 min and homogenize, t=65° C.

Cooling:

With stirring at 40° C., add preliminary solution of preservative in demin. water and perfume oil at 40° C. Then stir for 10 min and homogenize.

Cool to 30° C. with stirring and homogenization.

In comparison with the base without microparticles, the preparation according to the invention felt markedly creamier to the touch. An increase in viscosity was moreover observed.

TABLE 1

| Component | Comparisons | 1a | 1b | Comparisons | 2a | 2b |
|---|---|---|---|---|---|---|
| Sorbitan stearate | 1.50 | 1.50 | 1.50 | 1.50 | 1.50 | 1.50 |
| Polysorbate 60 | 2.00 | 2.00 | 2.00 | 2.00 | 2.00 | 2.00 |
| Cetyl alcohol | | | | 2.50 | 2.50 | 2.50 |
| Mineral oil | 8.00 | 8.00 | 8.00 | 8.00 | 8.00 | 8.00 |
| Decyl oleate | 4.00 | 4.00 | 4.00 | 4.00 | 4.00 | 4.00 |
| Glyceryl stearate | 4.00 | 4.00 | 4.00 | 5.00 | 5.00 | 5.00 |
| Dimethicone | 0.50 | 0.50 | 0.50 | 0.20 | 0.20 | 0.20 |
| Parabens | 0.35 | 0.35 | 0.35 | 0.35 | 0.35 | 0.35 |
| Completely deionized water (aqua) | 63.30 | 63.30 | 63.30 | 58.60 | 58.60 | 58.60 |
| Allantoin | 0.20 | 0.20 | 0.20 | 0.20 | 0.20 | 0.20 |
| Propylene glycol | 3.50 | 3.50 | 3.50 | 5.00 | 5.00 | 5.00 |
| Completely deionized water (aqua) | 10.00 | 8.00 | 5.00 | 10.00 | 8.00 | 5.00 |
| Microparticles* | | 2.00 | 5.00 | | 2.00 | 5.00 |
| Completely deionized water (aqua) | 2.00 | 2.00 | 2.00 | 2.00 | 2.00 | 2.00 |
| Imiazolidinyl urea | 0.50 | 0.50 | 0.50 | 0.50 | 0.50 | 0.50 |
| Perfume (fragrance) | 0.15 | 0.15 | 0.15 | 0.15 | 0.15 | 0.15 |
| | 100.00 | 100.00 | 100.00 | 100.00 | 100.00 | 100.00 |

*No INCI name

TABLE 2

| Component (INCI) | Comparisons 3 | 3a | 3b |
|---|---|---|---|
| Lanolin | 10.10 | 10.10 | 10.10 |
| Mineral oil | 7.85 | 7.85 | 7.85 |
| Castor oil | 2.80 | 2.80 | 2.80 |
| Octyldodecanol | 22.00 | 20.00 | 17.00 |
| Isopropyl palmitate | 5.00 | 5.00 | 5.00 |
| Antioxidant | 0.05 | 0.05 | 0.05 |
| PVP/eicosane copolymer | 0.15 | 0.15 | 0.15 |
| Iron oxide | 0.68 | 0.68 | 0.68 |
| Titanium dioxide* | 2.75 | 2.75 | 2.75 |
| Talc* | 16.07 | 16.07 | 16.07 |
| Mica | 13.90 | 13.90 | 13.90 |
| Microparticles* | | 2.00 | 5.00 |
| Cera microcritallina | 9.70 | 9.70 | 9.70 |
| Petrolatum | 7.65 | 7.65 | 7.65 |
| Carnauba | 1.30 | 1.30 | 1.30 |
| | 100.00 | 100.00 | 100.00 |

*No INCI name

TABLE 3

| Component INCI | Comparison 4 | 4a | 4b |
| --- | --- | --- | --- |
| Glyceryl stearate | 9.00 | 9.00 | 9.00 |
| Isopropyl myrisate | 2.25 | 2.25 | 2.25 |
| Cetyl alcohol | 1.50 | 1.50 | 1.50 |
| Parabens | 0.35 | 0.35 | 0.35 |
| Completely deionized water (aqua) | 62.27 | 62.27 | 62.27 |
| Allantoin | 0.25 | 0.25 | 0.25 |
| Xanthan gum | 0.30 | 0.30 | 0.30 |
| Propylene glycol | 8.90 | 8.90 | 8.90 |
| Iron oxide | 0.68 | 0.68 | 0.68 |
| Titanium oxide* | 2.75 | 2.75 | 2.75 |
| Completely deionized water (aqua) | 10.00 | 8.00 | 5.00 |
| Microparticles | | 2.00 | 5.00 |
| Perfume (fragrance) | 0.25 | 0.25 | 0.25 |
| Completely deionized water (aqua) | 1.00 | 1.00 | 1.00 |
| Imidazolidinyl urea | 0.50 | 0.50 | 0.50 |
| | 100.00 | 100.00 | 100.00 |

*No INCI name

EXAMPLE 5

Preparation of Microparticles from Poly-1,4-α-D-glucan 500 mg of poly-1,4-2-D-glucan are dissolved in 2.5 ml of dimethyl sulfoxide (DMSO, p.a. from Riedel-de-Haen) at about 70° C. The DMSO solution is added dropwise to 100 ml of double-distilled water with stirring and the solution is stored overnight at 5° C. The fine milky suspension is centrifuged at 3500 revolutions per minute for 15 minutes and the supernatant is decanted off. The sediment is suspended using double-distilled water and centrifuged again. The process is repeated a further two times. The suspension is then freeze-dried. 311 mg of white poly-1,4-α-D-glucan particles are obtained. This corresponds to a yield of 62% of colorless microparticles.

What is claimed is:

1. A topical preparation which comprises spherical microparticles wherein the spherical microparticles comprise at least one water-insoluble linear polyglucan having a degree of branching of not more than 0.5% in the 6-position.

2. The topical preparation as claimed in claim 1, wherein the microparticles have a mean diameter of from 1 μm to 100 μm.

3. The topical preparation as claimed in claim 1, wherein the depth of irregularities on the surface of the microparticle is at most 20% of the mean diameter of the microparticles.

4. The topical preparation as claimed in claim 1, wherein the microparticles are present in the topical preparation in an amount of from 0.5 to 80% by weight, based on the total weight of the topical preparation.

5. The topical preparation as claimed in claim 1, wherein the water-insoluble polyglucan is selected from the group consisting of poly-1,4-α-D-glucan, poly-1,3-β-D-glucan, and a mixture thereof.

6. The topical preparation as claimed claim 1, wherein the water-insoluble linear polyglucan is produced by a biotechnological method.

7. The topical preparation as claimed in claim 1, wherein the water-insoluble linear polyglucan is produced biocatalytically.

8. The topical preparation as claimed in claim 1, wherein the microparticles further comprise branched polysaccharides and further polymers.

9. The topical preparation as claimed in claim 1, wherein the microparticles comprise at least 70% of the at least one water-insoluble linear polyglucan based on the total content of polyglucan in the microparticle.

10. The topical preparation as claimed in claim 1, wherein the microparticles comprise 100% of the at least one water-insoluble linear polyglucan.

11. The topical preparation as claimed in claim 1, wherein the topical preparation is a cosmetic composition.

12. The topical composition as claimed in claim 1, wherein the cosmetic composition is a bodycare composition or a decorative cosmetic.

13. The topical preparation as claimed in claim 12, wherein the topical preparation is a decorative cosmetic selected from creams, powder and foundations for make-up.

14. The topical preparation as claimed in claim 13, wherein the make-up is rouge, eyeshadow or lipstick.

15. The topical preparation as claimed in claim 1, wherein the topical preparation is a human or veterinary medicinal preparation for external application.

16. The topical preparation as claimed in claim 1, wherein the topical preparation is selected from creams, compact creams, lotions, masks, powders, ointments, ointment bases and soaps.

17. A method of making a topical preparation comprising preparing spherical microparticles comprising at least one water-insoluble linear polyglucan.

18. The method of claim 17, wherein the at least one water-insoluble polyglucan has a degree of branching of less than 0.5% in the 6-position.

* * * * *